United States Patent [19]

Kastl et al.

[11] Patent Number: 4,488,435
[45] Date of Patent: Dec. 18, 1984

[54] ANALYSIS MANIPULATOR FOR NON-DESTRUCTIVE MATERIAL TESTING, AND METHOD FOR CONTROLLING THE COORDINATES THEREOF

[75] Inventors: Hans Kastl, Neustadt; Rainer Bauer, Herzogenaurach; Erich Modlich, Forchheim, all of Fed. Rep. of Germany

[73] Assignee: Kraftwerk Union Aktiengesellschaft, Mülheim, Fed. Rep. of Germany

[21] Appl. No.: 431,637

[22] Filed: Sep. 30, 1982

[30] Foreign Application Priority Data

Nov. 3, 1981 [DE] Fed. Rep. of Germany ....... 3143609

[51] Int. Cl.³ .............................................. G01V 29/00
[52] U.S. Cl. ........................................ 73/618; 73/619; 73/621; 414/749
[58] Field of Search ........................ 73/618, 619, 621; 414/749

[56] References Cited

U.S. PATENT DOCUMENTS

| | | | |
|---|---|---|---|
| 2,994,526 | 8/1961 | Clawson | 414/749 |
| 3,023,611 | 3/1962 | Howry | 73/621 |
| 3,118,254 | 1/1964 | DiLella | 414/749 |
| 3,910,124 | 10/1975 | Halsey | 73/618 |
| 4,170,145 | 10/1979 | Kennedy et al. | 73/620 |

OTHER PUBLICATIONS

"An Inexpensive Computer-Controlled Ultrasonic C-Scan System", Moghisi et al., NDT International, vol. 16, No. 1, Feb. 1983, pp. 9-12.

Primary Examiner—Howard A. Birmiel
Attorney, Agent, or Firm—Herbert L. Lerner; Laurence A. Greenberg

[57] ABSTRACT

Analysis manipulator for non-destructive material testing, including a support device having a mounting flange, a precision coordinate-moving mechanism having at least two guide frames each including coordinate drives in the form of straight guides and a drive having a spindle and a nut being movable by the spindle along the straight guides, the guide frames including a first lower guide frame having a mounting flange being mountable to the mounting flange of the support device, a second guide frame being movable by the coordinate drive of the first guide frame in a first given coordinate direction, and a testing head mount being movable by the coordinate drive of the second guide frame in a second given coordinate direction, and a method for the coordinate control of the analysis manipulator.

13 Claims, 4 Drawing Figures

ANALYSIS MANIPULATOR FOR NON-DESTRUCTIVE MATERIAL TESTING, AND METHOD FOR CONTROLLING THE COORDINATES THEREOF

The invention relates to an analysis manipulator for non-destructive material testing, particularly for carrying out test procedures, such as with focusing ultrasonic testing heads or according to the principle of acoustical holography, and furthermore to a method for controlling the coordinates of such an analysis manipulator, in which a constant distance from the respective extreme approach position is preselected and, when the preliminary switching-off point located ahead of the extreme position due to an inching selection is reached, the actual travel velocity is reduced to the inching velocity corresponding to a "start-stop" stepping frequency.

The manipulators used for routine, non-destructive repetitive or in-service tests, particularly with ultrasound, are constructed for remote-control positioning of ultrasonic search systems. Such tests have particular significance in nuclear power stations for determining the integrity of the components and in this connection, particularly for testing the primary loop with the associated primary loop components and pipelines. If the indications detected thereby exceed certain criteria they must be subjected to a special analysis. In this connection, essentially two test methods must be considered for determining the magnitude of the fault: firstly, focusing testing heads and secondly, acoustical holography (line and area holography). These analysis methods set requirements as to manipulator technology with respect to repeatable relative positioning accuracy and position resolution, which cannot be met by the heretofore-known devices. The invention begins at this point with an objective which is the development of an analysis manipulator, in which special requirements must be met. It should be possible to fasten the analysis manipulator to a carrier manipulator and to thereby transport it to roughly the position known from the search procedure. For analysis tests on the reactor pressure vessel from its inside, the central mast manipulator is to serve as the carrier manipulator. Depending on the area to be tested, it should be possible to mount the analysis manipulator to its horizontal outrigger (for the cylindrical pressure vessel region) or to the swivel arm thereof (for the spherical part of the pressure vessel). It follows therefrom that the analysis manipulator must be constructed in such a way as to be pressurized-water tight up to an immersion depth of about 30 m. Further important requirements are that the testing head of the analysis manipulator can be moved in two orthogonal directions with constant velocity across the maximum reading, and that any working position should be possible depending on the respective assembly position. It is a specific object of the invention to achieve a positioning accuracy of the testing head which is as high as possible relative to the carrier manipulator.

It is accordingly an object of the invention to provide an analysis manipulator for non-destructive material testing and a method for controlling the coordinates thereof, which overcomes the hereinaforementioned disadvantages of the heretofore known devices and methods of this general type, particularly for carrying out test procedures with focusing ultrasonic testing heads or according to the principle of acoustical holography, which meets the requirements described above.

It is further an object of the invention for the method of controlling the coordinates of such an analysis manipulator, to provide high approach accuracy.

With the foregoing and other objects in view there is provided, in accordance with the invention an analysis manipulator for non-destructive material testing, particularly for carrying out test procedures, such as with focusing ultrasonic testing heads or according to the principle of acoustical holography, comprising a carrier or other suitable support device having a mounting flange, a precision coordinate-moving mechanism having at least two guide frames each including coordinate drives in the form of straight guides and a drive having a spindle and nut being movable by the spindle along the straight guides, the guide frames including a first lower guide frame having a mounting flange being mountable to the mounting flange of the support device, a second guide frame being movable by the coordinate drive of the first guide frame in a first given coordinate direction, and a testing head mount or third guide frame being movable by the coordinate drive of the second guide frame in a second given coordinate direction.

In accordance with another feature of the invention the straight guides of the first and second guide frames are in the form of guide rods and ball bearing bushings associated therewith.

In accordance with an additional feature of the invention the guide rods of the first guide frame are drilled hollow.

In accordance with still an added feature of the invention, the spindles are rotary ball spindles.

In accordance with a further feature of the invention there is provided d or c multiphase stepping drive motors, particularly 5-phase stepping motors, connected to the rotary ball spindles.

In accordance with an additional feature of the invention, the rotary ball spindles have two ends, one of the ends being connected to the motors, and including incremental angular momentum transmitters connected to the other of the ends of the rotary ball spindles, facing away from the motors.

In accordance with another added feature of the invention there are provided hood-like pressurized water-tight protective housings for the connections of the stepping motors to the guide frames and rotary ball spindles for deployment under water, and cooling ribs disposed on the housings.

In accordance with yet a further feature of the invention there are provided pressure-tight hood-like protective housings enclosing the angular momentum transmitters.

In accordance with another feature of the invention the housings have shaft leadthroughs formed therein for the rotary ball spindles, and including pillow-blocks having pretensioned sliding ring seals therein and additional protective covers sealing and protecting the housings against shock in vicinity of the shaft leadthroughs.

In accordance with still an added feature of the invention the housings have cable feedthroughs formed therein, and including a pressure-proof casting filling the cable feedthroughs.

In accordance with yet an additional feature of the invention the guide frames are movable through strokes in the given directions, and including water-tight end switches limiting the strokes at two ends in the given directions, the switches being responsive without contact, as adjusting or reference point switches.

In accordance with still a further feature of the invention there is provided a series switch upstream of each of the end switches for reducing the actual travel velocity to an inching velocity and for providing an exact approach to the end switches independent of the testing speed.

In accordance with another feature of the invention the mounting flange of the first guide frame is mountable in any desired or arbitrary stepwise angle of orientation relative to the mounting flange of the support device.

In accordance with another added feature of the invention the testing head mount includes a mounting frame, a testing head supported in gimbal joints, and a spring loaded double rocker linking the testing head to the mounting frame according to the Evans steering principle.

In accordance with yet a further feature of the invention, the second guide frame has a mounting surface, and the mounting frame is mountable on the mounting surface in any desired or arbitrarily graduated angle of orientation.

In accordance with the objects of the invention there is also provided a method for controlling the coordinates of the analysis manipulator, which includes preselecting extreme approach positions for the second guide frame and the testing head mount, preselecting a constant distance from the respective extreme approach position, preselecting a preliminary switching-off point upstream of the extreme position, and reducing the actual travel velocity of the second guide frame and the testing head mount to an inching velocity corresponding to a start-stop stepping frequency when the preliminary switching-off point is reached due to the inching selection.

In accordance with another mode of the invention, there is provided a method which includes separately adjusting the travel velocity for each given coordinate axis direction without steps, particularly between 2 and 30 mm/s, and indicating the travel velocity at a control station.

In accordance with a concomitant mode of the invention, there is provided a method which includes moving each of the coordinate drives in a step operating mode, in which the coordinate drives each execute a preselected step-width upon the pressure of a key, independently of the duration of pressure on the key, in addition to automatic program cycles and inching and continuous operating modes.

The advantages attainable with the invention are seen particularly as follows: It is possible to increase the positioning accuracy relative to the carrier manipulator to ±0.2 mm with a position resolution of 0.01 mm. These properties, which far exceed the standards applicable to test manipulators (positioning accuracy ±1.5 mm) could be achieved through great stiffness of the manipulator structure which, however, because of the limited load-carrying capacity of the carrier manipulators on one hand, and the difficulty in handling during installation on the other hand, must be achieved with a minimum weight. It is possible to achieve these properties with a testing head stroke in two travel directions x and y of 300 mm each (= ±150 mm) according to the maximum aperture length. The specified positioning accuracy applies to the entire system of the analysis manipulator and also takes into consideration permissible position deviation of the testing head mounting.

Other features which are considered characteristics for the invention are set forth in the appended claims.

Although the invention is illustrated and described herein as embodied in an analysis manipulator for nondestructive material testing, and method for controlling the coordinates thereof, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which.

Figure 1:
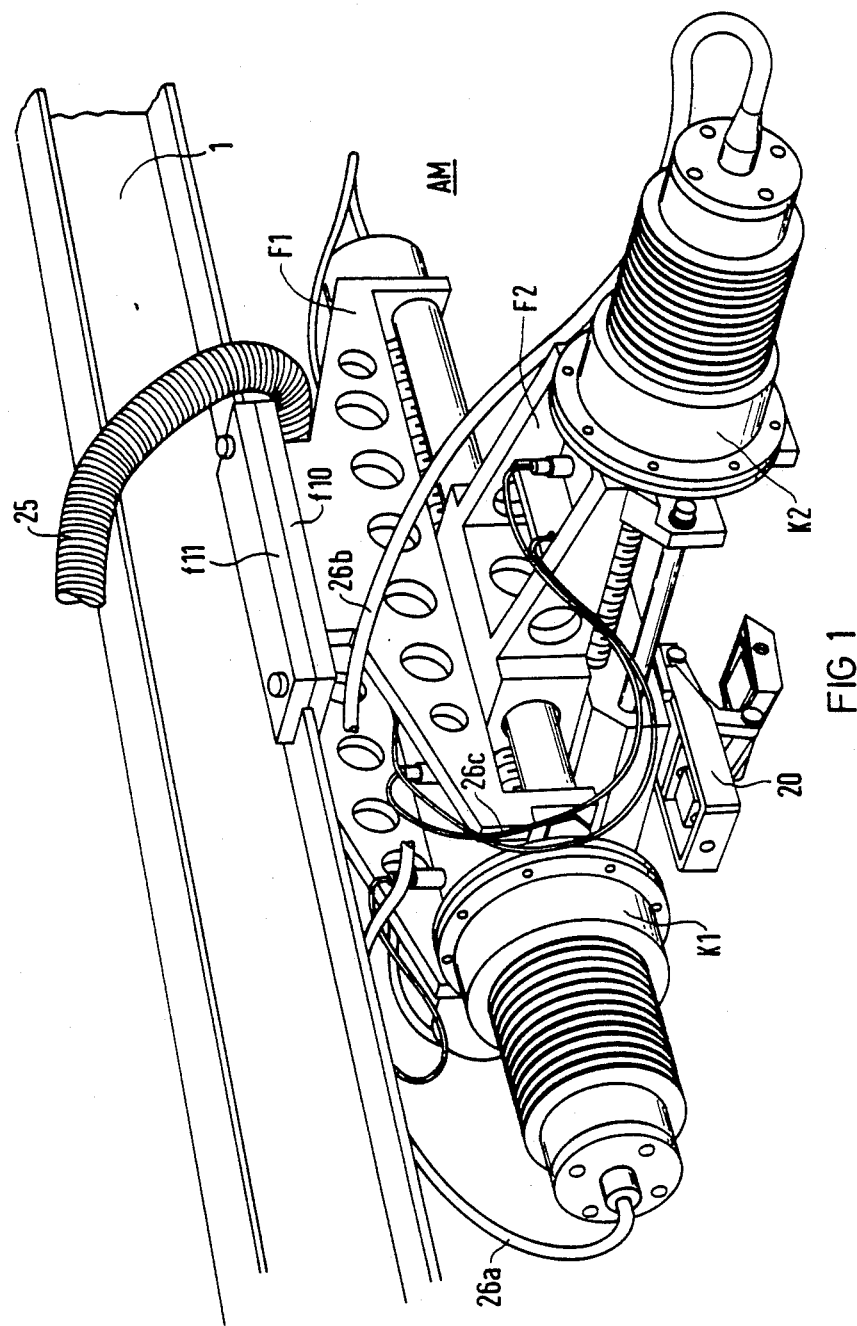
FIG. 1 is a diagrammatic perspective view of the analysis manipulator of the invention, fastened to a support bar which generally may be the support organ or the outrigger of a carrier manipulator.
Figure 2:
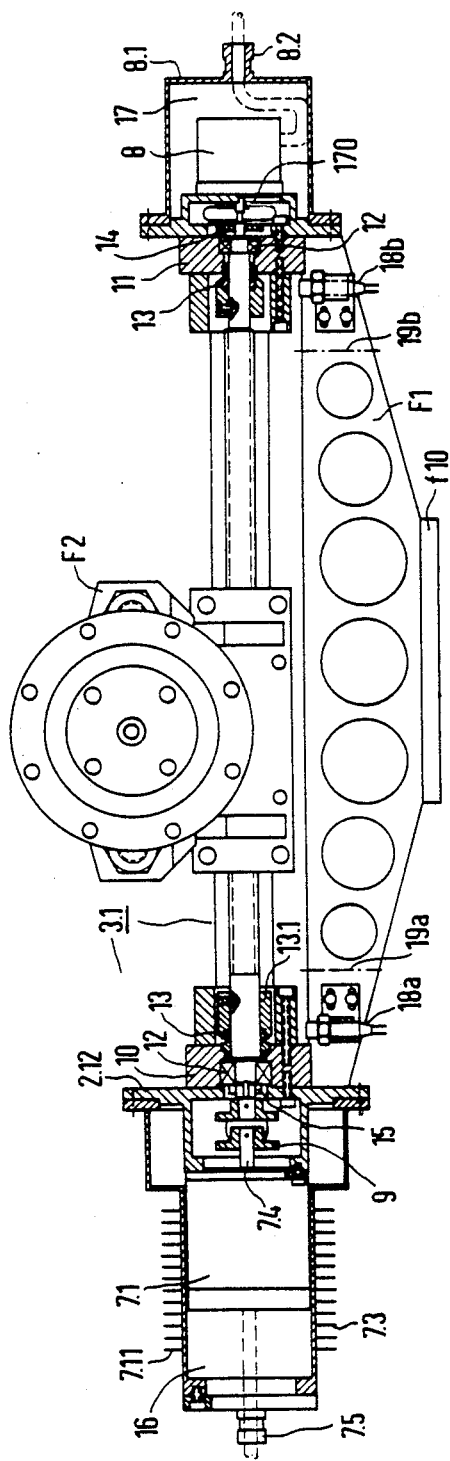
FIG. 2 is a front elevational view of FIG. 1.
Figure 3:
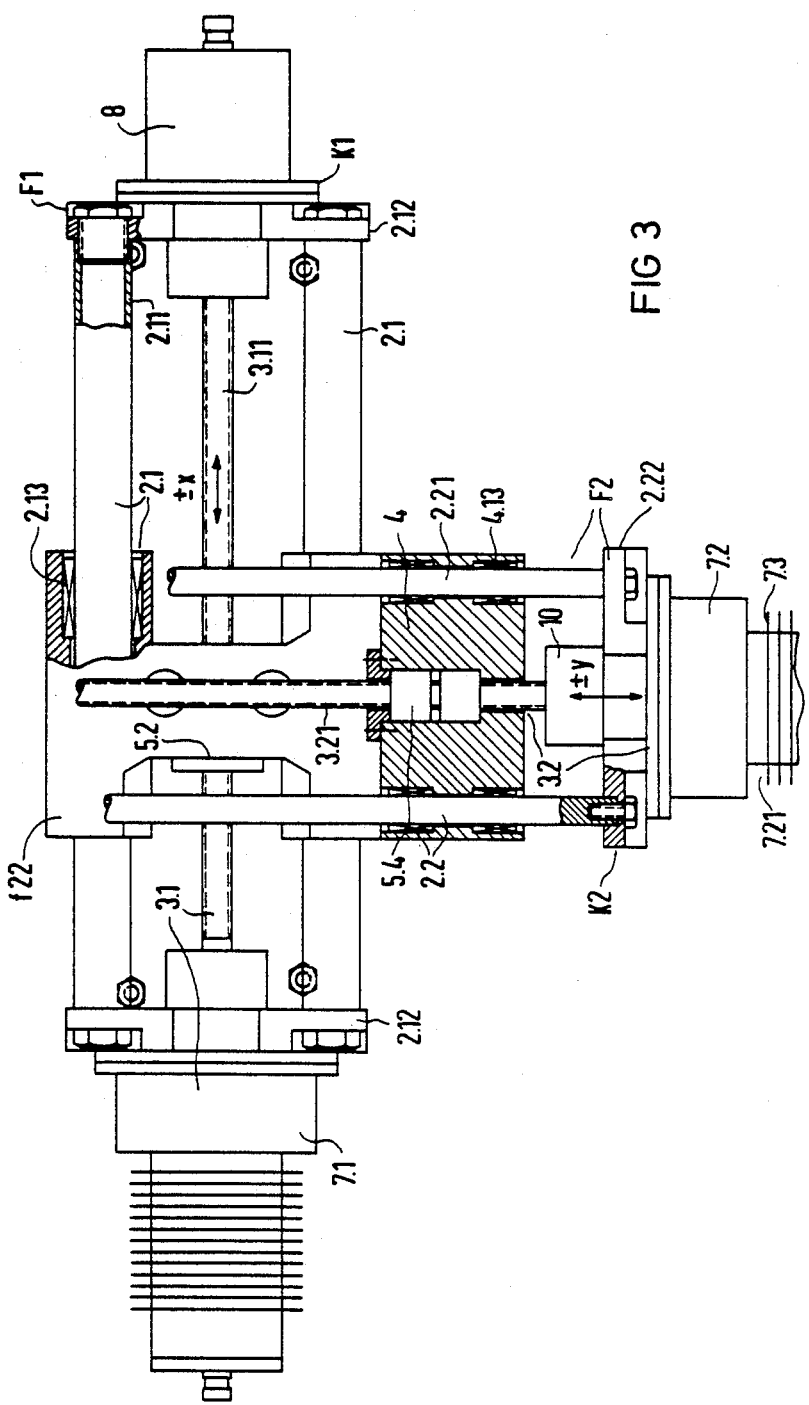
FIG. 3 is a top plan view partially in cross section and broken away, of the analysis manipulator according to FIG. 1.
Figure 4:
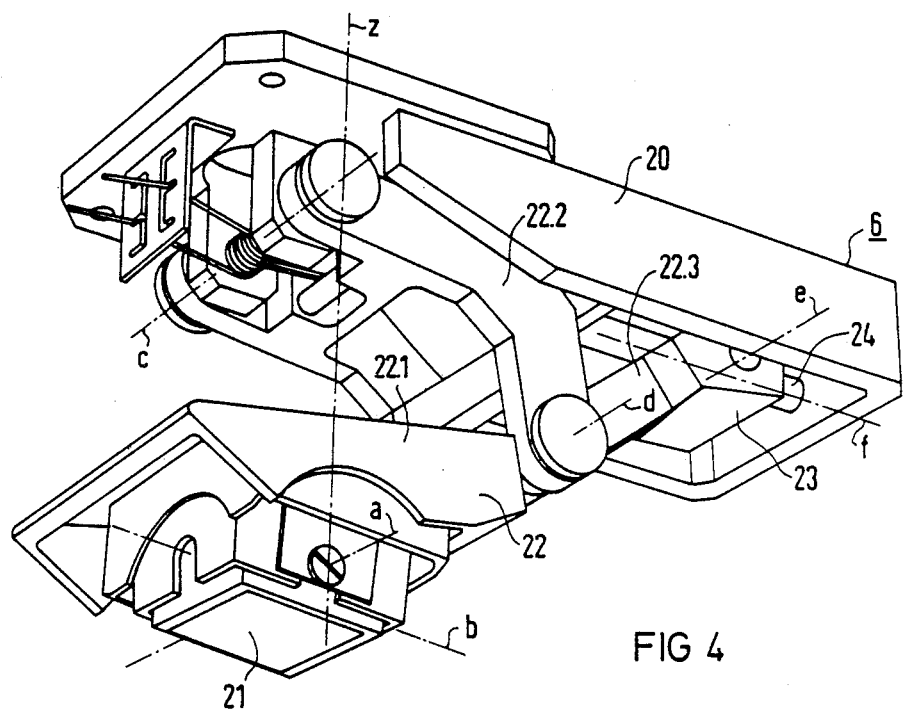
FIG. 4 is another perspective view of a testing head mounting which can be fastened to the second guide frame of the invention.

Referring now to the figures of the drawing and first particularly to FIG. 1 thereof, it is seen that the analysis manipulator, designated with reference character AM, as a whole, includes a precision coordinate positioning mechanism with two guide frames F1 and F2 which are each equipped with a coordinate drive K1 and K2, respectively. The first lower guide frame F1 is clamped to a beam 1 by way of a base plate or mounting flange f10 thereof and a double-jaw mounting flange f11 fastened thereto. The beam 1 can generally be the mounting flange of a non-illustrated carrier manipulator. Each of the coordinate drives K1, K2 has two straight guides 2.1, 2.2, respectively, with a spindle/travelling-nut drive 3.1, 3.2, respectively, as is shown in FIGS. 2 and 3 in conjunction with FIG. 1. The second guide frame F2 can be moved, by means of the coordinate drive K1 of the first guide frame F1, relative to the first guide frame F1 in a first coordinate direction ±x seen in FIG. 3. Furthermore, at the second guide frame F2, a support 4 of a further guide frame or a testing head mount 20, shown in FIGS. 1 and 4, can be moved by means of the coordinate drive K2 in a second coordinate direction ±y seen in FIG. 3.

In detail, the straight guides 2.1, 2.2 are formed of guide rods 2.11, 2.21, respectively, which are bolted with their ends to mounting flanges 2.12, 2.22 of the guide frames F1, F2, and of associated ball bearing bushings or sleeves 2.13, 4.13. In this way, supports f22 of the second guide frame F2 and the support 4, respectively, of the testing head mounting 20 are supported in such a way as to be movable in the lengthwise direction on the guide rods 2.11. The guide rods 2.11 of the first guide frame F1 are hollow for weight reasons, but the guide rods 2.21 are not hollow, since their diameter is only approximately one half of that of the guide rods 2.11. The spindle/travelling-nut drives 3.1 and 3.2 have so-called rotary ball spindles 3.11 and 3.21, respectively, which can revolve in double travelling nuts 5.2 and 5.4, respectively, that are disposed in such a way as to be secured against rotation but axially movable with their supports f22 and 4, respectively. In this way, the support f22 with the entire guide frame F2 can be moved in the ±x direction and the support 4 with the testing head mount 20, (which is not shown in FIGS. 2 and 3) can be moved in the ±y direction, if a drive motor 7.1 for the spindle 3.11 and a drive motor 7.2 for the spindle 3.21, respectively, are rotating.

The drive motors 7.1, 7.2 are preferably multiphase stepping motors, particularly 5-phase stepping motors because with these motors, a very finely graduated or a continuous adjustment of the desired speed is possible. Connected to the ends of the rotary ball spindles 3.11 and 3.21 are incremental angular momentum transmitters 8 which are enclosed in a pressure-proof manner by hood-like protective housings 8.1. Only the transmitter 8 for the spindle 3.11 is illustrated in the drawings. The housing 8.1 is pressure-tightly bolted to the mounting flange 2.12 and has a cable feedthrough stub 8.2. The drive motors 7.1, 7.2 are also enclosed by protective housings 7.11, 7.21 which are constructed like hoods and are provided with cooling fins 7.3. The coupling of a motor shaft 7.4 to the spindle 3.11 and correspondingly, the coupling between the spindle 3.21 and the associated motor shaft, is accomplished via an Arpex coupler 9 as shown in FIG. 2. The protective housing 7.11 also has a cable feedthrough stub 7.5. A pillow block 10 for the end of the spindle 3.11 on the motor side is connected in a sealed manner to the mounting flange 2.12 of the guide frame F1; a correspondingly constructed hollow cylindrical pillow block at the end of the spindle 3.11 on the angular momentum transmitter side is designated with reference numeral 11. Similar bearing blocks 10 and non-illustrated bearing blocks 11 are also provided for the spindle 3.21. Ball bearings inside the bearing blocks 10, 11 are designated with reference numeral 12 and pretensioned sliding ring seals for the spindle 3.11 are designated with reference numeral 13. The spindle 3.11 (and correspondingly, the spindle 3.21) is fixed in the axial direction by a securing ring 14 at the support bearing 12 of the bearing block 11 on one hand, and by a shaft nut with a securing sheet-metal part 15 at the support bearing 12 of the bearing block 10, on the other hand.

The cable feedthroughs 7.5, 8.2 are cast in such a way as to be full and pressure tight, i.e. spaces 16 and 17 in the hood can be filled completely with hardening synthetic resin; however, sufficient heat transfer area must be left for the motor 7.1. The spindle 3.11 is coupled to the transmitter 8 by a cupspring coupler 170.

The excursions of the supports f22 and 4 in the respective coordinate directions are limited on both sides by watertight, contactless end switches 18a, 18b which serve as adjustment or reference-point switches. Only the end switches 18a, 18b for the support f22 which are fastened to the first guide frame F1 in the vicinity of the two desired extreme positions, are visible. These end switches may each be preceded by one series switch as indicated by the dot-dash lines at 19a, 19b, in order to reduce the respective actual travelling velocity of the supports to an inching velocity, so that the end switches can be approached exactly and independently of the testing speed.

The mounting of the analysis manipulator AM parallel to the beam 1 with its first guide frame F1, as indicated in FIG. 1, is not the only possiblility; it can rather be mounted with its mounting flange in any desired or arbitrarily graduated angle orientation with respect to the mounting flange 11. The same applies to the fastening of the testing head mount 20 at the support 4, shown in FIG. 4. The testing head mount 20 has a mounting frame, to which a gimbal-supported testing head 21 is linked through a spring-loaded double rocker 22 according to the Evans steering principle. The two gimbal axes of the testing head 21 are designated with reference characters a and b, the lever arm of the double rocker 22 are given reference numerals 22.1 and 22.2, and their two pivots are designated with reference characters c and d. Spiral springs are disposed at these pivot axes c, d, which load the double rocker 22 in the sense of pressing the testing head 21 against the substrate to be examined. The testing head 21 always remains in the same vertical plane if the surface is uneven, and is sprung upward or downward. According to the Evans steering principle, this is achieved by the provision that an extension 22.3 of the lever arm 22.1 is linked to a sleeve 23 rotatably about an axis of rotation e. The sleeve 23 is supported on a post 24 connected to the frame of the testing head mount 20 so that it is movable lengthwise in a direction f. This particularly advantageous testing head mounting is described in German Published, Non-Prosecuted Application DE-OS 29 35 497 and therefore need not be explained in detail herein.

As will be seen, the two guide frames F1, F2 of the analysis manipulator AM are constructed in a largely symmetrical and weightsaving manner. The drive motors 7.1, 7.2 for the x and y axes which are identical for redundancy reasons and are, in particular, 5-phase stepping motors, have a remarkably uniform rotation behavior in the stepping frequency utilized. While omitting intermediate transmissions, at the same time, a large holding torque is provided at standstill by the type of coupling chosen (the Arpex coupling 9) to the spindle 3.11 and 3.21, respectively. With the incremental angular momentum transmitter 8 (and the one associated with the spindle 3.21), the actually executed motion of the support 4, and therefore of the testing head mount 20, can be determined. One pulse always corresponds to a travel distance of 0.01 mm.

The analysis testing head 21, which is a focusing testing head, is supported, as already mentioned in such a way that its coupling surface optimally follows the testing surface and its reference center does not unpermissibly deviate from the indicated position x/y even in the event of spring excursions that may be necessary. The gimbal support of the testing head 21 is disposed in such a way that it swivels about the center of the sphere placed in the coupling plane. The spiral springs associated with the pivots c and d can be adjusted in six steps.

FIG. 1 further shows a water-tight overall cable assembly 25 on the manipulator side, which has, for instance, a length of 30 m for testing work under water. The individual cables 26a for the motors, 26b for the positioning transmitters and 26c for the end switches which are each disposed in protective tubing, are individually relieved of tension, intentionally avoiding water-tight connectors at the manipulator AM. In addition, the entire assembly 25 is secured by means of a non-illustrated tension relief clamp.

A non-illustrated control device which is connected through the overall cable assembly, a connector junction box and connecting cables which may be 20 m long, for instance, and lead to the analysis manipulator, is constructed as a transportable cabinet. The control device includes electronic power circuits for the 5-phase stepping motors, position counters with indicator panels, logic electronics, as well as all command push buttons and control lights. With their aid, the analysis manipulator can be remotely controlled. The actual position of each coordinate is indicated at the front panel, for instance, with six digits in one-hundredths of a millimeter. The respective extreme positions ($x_{min}$; $x_{max}$; $y_{min}$; $y_{max}$) can be preselected by coding switches. The spacing of the parallel testing tracks (x and y, respectively) can likewise be set. A constant distance from the respective extreme position can also be preselected. When the preliminary switching-off point, which is located ahead of the extreme position by this inching selection is reached, the actual travel velocity is reduced to the inching speed corresponding to the "start-stop" stepping frequency. With a sufficiently chosen inching preselection, an actual position exactly corresponding to the desired position at the end of the travel track is possible. In particular, in this case the travel speed is continuously and separately set for the coordinate axes, preferably between 2 mm/s and 30 mm/s, and is indicated at a control station, preferably digitally.

The different automatically traversed travel figures can be called up as hard-wired programs through the respectively assigned pushbutton. In detail, the following travel figures are possible:

Horizontal meander, vertical meander, one-way cycle and cross cycle. In addition to these automatic program cycles, and in addition to an inching and continuous mode of operation, each of the coordinate drives K1, K2 can be moved in the stepping operation mode, in which the coordinate drives execute a respectively preselected step width upon pressing a key, independently of the duration of the key pressure. This mode of operation enables the operator to advance the respective testing axis by an adjustable amount, namely the step width, such as for "growing indications". This stepping operation is independent of skill.

The foregoing is a description corresponding to German Application No. P 31 43 609.9, dated Nov. 3, 1981, the International Priority of which is being claimed for the instant application and which is thereby made part of this application. Any discrepancies between the foregoing specification and the aforementioned corresponding German application are to be resolved in favor of the latter.

We claim:

1. Manipulator for positioning a testing head for non-destructive material testing of tanks and pipelines in the primary loop of nuclear power plants, comprising a testing head support device, a coordinate-moving mechanism including a first guide frame with a first coordinate drive and a second guide frame with a second coordinate drive, each of said coordinate drives including straight guides and a drive, said drives having a spindle with two opposite ends, a nut being movable by said spindle along said straight guides and rotating balls disposed between said nut and said spindle, a mounting flange connecting said first guide frame to said testing head support device, said second guide frame being movable by said first coordinate drive, a testing head mount supporting the testing head and being movable by said second coordinate drive, multiphase stepping motors each being connected to one end of a respective one of said spindles, and incremental rotarty motion transmitters each being connected to the other end of a respective one of said spindles for transmitting the actual rotary position of said spindles to control devices outside the manipulator.

2. Analysis manipulator according to claim 1, wherein said straight guides of said first and second guide frames are in the form of hollow guide rods and ball bearing bushings associated therewith.

3. Analysis manipulator according to claim 1, including hood-like pressurized water-tight protective housings for said connections of said motors to said guide frames and rotary ball spindles, and cooling ribs disposed on said housings.

4. Analysis manipulator according to claim 3, wherein said housings have shaft leadthroughs formed therein for said spindles, and including bearing blocks having pretensioned sliding ring seals and additional protective covers sealing and protecting said housings against shock in vicinity of said shaft leadthroughs.

5. Analysis manipulator according to claim 3, wherein said housings have cable feedthroughs formed therein, and including a pressure-proof casting filling said cable feedthroughs.

6. Analysis manipulator according to claim 1, including pressure-tight hood-like protective housings enclosing said angular momentum transmitters.

7. Analysis manipulator according to claim 6, wherein said housings have shaft leadthroughs formed therein for said spindles, and including bearing blocks having pretensioned sliding ring seals and additional protective covers sealing and protecting said housings against shock in vicinity of said shaft leadthroughs.

8. Analysis manipulator according to claim 6, wherein said housings have cable feedthroughs formed therein, and including a pressure-proof casting filling said cable feedthroughs.

9. Analysis manipulator according to claim 1, wherein said guide frames are movable through strokes in given directions, and including water-tight end switches limiting said strokes at two ends in given directions, said switches being responsive without contact.

10. Analysis manipulator according to claim 9, including a series switch upstream of each of said end switches for reducing the actual travel velocity to an inching velocity and for providing an exact approach to said end switches independent of the testing speed.

11. Method for the coordinate control of an analysis manipulator, including a support device having a mounting flange, a precision coordinate-moving mechanism having at least two guide frames each including coordinate drives in the form of straight guides and a drive having a spindle and a nut being movable by the spindle along the straight guides, the guide frames including a first lower guide frame having a mounting flange being mountable to the mounting flange of the support device, a second guide frame being movable by the coordinate drive of the first guide frame in a first given coordinate direction, and a testing head mount being movable by the coordinate drive of the second guide frame in a second given coordinate direction, which comprises preselecting extreme approach positions for the second guide frame and the testing head mount, preselecting a constant distance from the respective extreme approach position, preselecting a preliminary switching-off point upstream of the extreme position, and reducing the actual travel velocity of said second guide frame and said testing head mount to an inching velocity corresponding to a start-stop stepping frequency when the preliminary switching-off point is reached.

12. Method according to claim 11, which comprises separately adjusting the travel velocity for each given coordinate direction without steps, and indicating the travel velocity at a control station.

13. Method according to claim 11, which comprises moving each of the coordinate drives in a step operating mode, in which the coordinate drives each execute a preselected step-width operating a key button, independently of the duration of the operation of the key button.

* * * * *